(12) United States Patent
Boast

(10) Patent No.: US 9,157,900 B2
(45) Date of Patent: Oct. 13, 2015

(54) SYSTEM AND METHOD FOR MONITORING THE ATMOSPHERE OF AN ANAEROBIC WORKSTATION

(75) Inventor: David Boast, West Yorkshire (GB)

(73) Assignee: Don Whitley Scientific Limited, West Yorkshire (GB)

( * ) Notice: Subject to any disclaimer, the term of this patent is extended or adjusted under 35 U.S.C. 154(b) by 374 days.

(21) Appl. No.: 13/697,680

(22) PCT Filed: Oct. 24, 2011

(86) PCT No.: PCT/GB2011/000790
§ 371 (c)(1),
(2), (4) Date: Nov. 13, 2012

(87) PCT Pub. No.: WO2011/148129
PCT Pub. Date: Dec. 1, 2011

(65) Prior Publication Data
US 2013/0059390 A1    Mar. 7, 2013

(30) Foreign Application Priority Data

May 25, 2010    (GB) .................................. 1008716.1

(51) Int. Cl.
*G01N 31/10*    (2006.01)
*G01N 25/22*    (2006.01)
(Continued)

(52) U.S. Cl.
CPC ................ *G01N 31/10* (2013.01); *C12M 41/34* (2013.01); *G01N 25/22* (2013.01); *G01N 25/48* (2013.01)

(58) Field of Classification Search
CPC ....... G01N 31/10; G01N 25/22; G01N 25/48; C12M 41/34
USPC .............. 422/51, 83; 312/1; 436/37, 147, 159
See application file for complete search history.

(56) References Cited

U.S. PATENT DOCUMENTS 3,488,155 A * 1/1970 Ayers ........................... 436/147
4,033,826 A * 7/1977 Larsen et al. .............. 435/303.2
(Continued)

FOREIGN PATENT DOCUMENTS

| EP | 0089830 | 9/1983 |
|---|---|---|
| JP | 9113481 | 5/1997 |
| JP | 2000241375 | 9/2000 |

OTHER PUBLICATIONS

International Search Report for Application No. PCT/GB2011/000790 dated Sep. 5, 2011 (2 pages).

*Primary Examiner* — Arlen Soderquist
(74) *Attorney, Agent, or Firm* — Michael Best & Friedrich LLP

(57) ABSTRACT

Aspects of the invention relates to a system and method for determining the efficacy of the catalyst comprising means to detect any temperature change in the catalyst when oxygen is present in the anaerobic workstation and determine the efficacy of the catalyst in accordance with the temperature change. A detectable rise in the temperature of the catalyst is indicative of a catalytic reaction to remove oxygen from the anaerobic work station. Thus, the system determines the catalyst is an active catalyst if the temperature of the catalyst rises when oxygen is present in the anaerobic workstation. The system determines the catalyst is an inactive catalyst if the temperature of the catalyst does not rise when oxygen is present in the anaerobic workstation. Further aspect of the invention relate to a system and method for determining the atmosphere of an anaerobic workstation in accordance with the efficacy of the catalyst of the anaerobic workstation.

20 Claims, 4 Drawing Sheets

(51) Int. Cl.
*G01N 25/48* (2006.01)
*C12M 1/34* (2006.01)

(56) References Cited

U.S. PATENT DOCUMENTS

| | | | |
|---|---|---|---|
| 4,111,753 A * | 9/1978 | Folsom et al. | 435/3 |
| 4,169,708 A * | 10/1979 | Muggli | 436/136 |
| 4,170,455 A * | 10/1979 | Henrie | 436/144 |
| 4,262,091 A * | 4/1981 | Cox | 435/253.6 |
| 4,289,855 A * | 9/1981 | Whitley | 435/303.2 |
| 4,686,188 A * | 8/1987 | Whitley | 435/260 |
| 4,755,355 A | 7/1988 | Coy et al. | |
| 4,891,464 A * | 1/1990 | Staggs | 585/440 |
| 4,976,931 A * | 12/1990 | Stoermer et al. | 422/211 |
| 5,057,285 A * | 10/1991 | Belt et al. | 422/236 |
| 5,060,473 A * | 10/1991 | Nakagawa | 60/277 |
| 5,132,082 A * | 7/1992 | Simkovich et al. | 419/57 |
| 5,219,755 A * | 6/1993 | Willemot et al. | 435/243 |
| 5,339,628 A * | 8/1994 | Maus et al. | 60/277 |
| 5,922,287 A * | 7/1999 | Kato et al. | 422/95 |
| 6,063,633 A * | 5/2000 | Willson, III | 436/37 |
| 6,651,422 B1 * | 11/2003 | LeGare | 60/277 |
| 2002/0197721 A1 * | 12/2002 | Kinugawa et al. | 436/37 |
| 2004/0128983 A1 * | 7/2004 | Okada et al. | 60/277 |

\* cited by examiner

SYSTEM AND METHOD FOR MONITORING THE ATMOSPHERE OF AN ANAEROBIC WORKSTATION

FIELD OF INVENTION

The present invention relates to a system and method for determining the efficacy of a catalyst used to remove oxygen from an atmosphere by reaction with hydrogen. In particular, though not exclusively, the present invention may be applied to anaerobic workstations that utilize a catalyst for the removal of oxygen from the atmosphere of the workstation.

BACKGROUND ART

An anaerobic organism or anaerobe is an organism that does not require oxygen to grow, may react adversely to the presence of oxygen and, if particularly sensitive, may die if exposed to a small amount of oxygen.

Since air consists of approximately 20% oxygen and 80% nitrogen, it is essential to cultivate anaerobes in a sealed vessel whose environmental conditions are controlled.

An anaerobic workstation is typically used to cultivate anaerobes. Anaerobic workstations comprise a sealed chamber and means to regulate the atmosphere, temperature and humidity as required. Anaerobe samples or cultures can be introduced, manipulated, incubated and examined in an anaerobic workstation without disturbing the environmental conditions and without exposing the anaerobes to atmospheric oxygen until they are removed from the anaerobic workstation.

Anaerobic workstations are suitable for use in a number of different industries and applications. For example, anaerobic culture stations are used in microbiology laboratories where there is a need to easily process, culture and examine microbiological samples without exposure to atmospheric oxygen.

An anaerobic workstation is supplied with an anaerobic gas mixture so as to provide an anaerobic atmosphere. The anaerobic gas mixture includes hydrogen gas. The hydrogen gas is provided to help to create and maintain the anaerobic conditions by combining with any oxygen in the atmosphere of the workstation. The hydrogen combines with oxygen in the presence of a catalyst. During the catalytic reaction, the hydrogen and oxygen combine in a ratio of 2:1 so as to form water vapour. The catalytic reaction is an exothermic reaction.

An anaerobe sample stored within an anaerobic workstation may be irreplaceably lost if the anaerobic atmosphere of the workstation is compromised. So as to maintain the stringent anaerobic conditions, it is necessary to ensure the ratio of hydrogen to oxygen is at least 2:1 and the catalyst is an active catalyst; i.e. a catalyst that has the efficacy (capacity) to initiate a catalytic reaction that is sufficient to remove any oxygen present in the workstation.

It is known and understood that the catalyst of an anaerobic workstation may degrade during use. This has the effect of slowing the rate of catalytic reaction and thereby the rate at which oxygen is removed from the workstation. The rate at which heat is generated during the sluggish catalytic reaction is also correspondingly reduced. If the catalyst fails during use then no catalytic reaction can occur to remove oxygen and the anaerobic conditions of the anaerobic workstation are therefore comprised. Accordingly, the catalyst is regularly replaced in anaerobic workstations so as to try and avoid degradation or failure of the catalyst.

So as to determine if the anaerobic condition is being maintained, anaerobic workstations may additionally comprise means to sense the presence or absence of oxygen. For example, control organisms may be utilized to confirm whether or not appropriate anaerobic conditions exist in an anaerobic workstation. Sensitive organism that will only grow in the absence of oxygen may be used as a positive control. Conversely, organisms that require the presence of oxygen to flourish may be used as a negative control. Control organisms provide an accurate and consistent confirmation that appropriate anaerobic conditions exist or have been compromised. However, there is often an undesirable time lag between a detectable result to alert a workstation user that the anaerobic atmosphere has been lost and this time lag may lead to the loss of samples. Moreover, the use of control organisms is labour intensive and can be expensive.

Others methods of detecting the atmosphere of an anaerobic workstation include the use of gas sensing means. For example, an anaerobic workstation may be provided with an oxygen sensor. Gas sensors are capable of reliable operation and rapidly detect the presence or absence of a gas. However, oxygen sensors that are capable of detecting the presence or absence of very low levels of oxygen can be expensive, can be adversely affected by the presence of other gases and/or compounds present in anaerobic environments, or experience unacceptable levels of drift thereby affecting accuracy over time.

SUMMARY OF THE INVENTION

Embodiments of the invention seek to address and/or overcome one or more of the problems addressed above. Embodiments of the invention seek to provide a system and method for determining the efficacy of the catalyst. Embodiments of the invention seek to provide a system and method for determining the atmosphere of an anaerobic workstation in accordance with the efficacy of the catalyst in the anaerobic workstation. More generally, embodiments of the invention provide a system and method for determining the efficacy of a catalytic reaction.

The first aspect of the invention relates to a system for determining the efficacy of a catalyst used to remove oxygen from an atmosphere by reaction with hydrogen, comprising means to detect any temperature change in the catalyst when oxygen is present in the atmosphere and determining the efficacy of the catalyst in accordance with the temperature change.

A detectable rise in the temperature of the catalyst is indicative of a catalytic reaction to remove oxygen from the atmosphere. Thus, the system determines the catalyst is an active catalyst if the temperature of the catalyst rises when oxygen is present in the atmosphere. The system determines the catalyst is an inactive catalyst if the temperature of the catalyst does not rise when oxygen is present.

The system for determining the efficacy of the catalyst may comprise:

temperature sensing means for sensing the temperature of the catalyst;

control means for processing the temperature data of the temperature sensing means and for determining the efficacy of the catalyst in accordance with any temperature change of the catalyst when oxygen is present.

The temperature sensing means may comprise a temperature sensing probe locatable in the catalyst. The temperature sensing probe may be a temperature sensing probe substantially centrally locatable in the catalyst.

The control means may comprise computer control means to process temperature data from the temperature sensing means and determine the efficacy of the catalyst based on any temperature change of the catalyst.

The control means may be configured to determine the catalyst is an active catalyst if the temperature sensing means detect a rise in catalytic temperature when oxygen is present. The control means may be configured to determine the catalyst is an inactive catalyst if the temperature sensing means do not detect a rise in catalytic temperature when oxygen is present.

A catalyst with a substantially high efficacy will change temperature at a substantially higher rate during the catalytic reaction. The control means may therefore be configured to determine the catalyst is an active catalyst with a substantially high efficacy if the temperature of the catalyst rises above a first predetermined temperature, if the temperature of the catalyst increases by at least a first predetermined rate of temperature when oxygen is present.

A catalyst with a substantially low efficacy will change temperature at a substantially lower rate during the catalytic reaction. The control means may be configured to determine the catalyst is an active catalyst with a substantially low (reduced) efficacy if the temperature of the catalyst rises to at least a second predetermined temperature that is lower than the first predetermined temperature, if the temperature of the catalyst rises by up to a second predetermined amount that is less than the first predetermined temperature amount or if the temperature of the catalyst increases by up to a second predetermined rate of increase that is slower than the first predetermined rate when oxygen is present.

An inactive catalyst will not change in temperature because it will not undergo a catalytic reaction when oxygen is present in the atmosphere. The control means may be configured to determine the catalyst is an inactive catalyst if the temperature of the catalyst does not rise above a nominal temperature when oxygen is present.

The computer control means may comprise a programmable logic controller.

The system may further comprise display means to indicate the efficacy status of the catalyst. The display means may comprise means for indicating the catalyst is an active catalyst or an inactive catalyst. The display means may comprise means for indicating the catalyst is an active catalyst with a substantially high efficacy, the catalyst is an active catalyst with a substantially low (reduced) efficacy or the catalyst is an inactive catalyst.

The display means may comprise a computer display screen. The computer display screen may be a touch screen.

A second aspect of the system relates to a method of determining the efficacy of a catalyst used to remove oxygen from an atmosphere by reaction with hydrogen, the method comprising the steps of:— measuring the temperature of the catalyst; and determining the efficacy of the catalyst in accordance with any temperature change of the catalyst when oxygen is present in the atmosphere.

Preferably, the method further comprises the step of using a system according to the first aspect of the invention to determine the efficacy of the catalyst.

A third aspect of the invention relates to a system for monitoring the atmosphere of an anaerobic workstation, the system comprises:

a system for determining the efficacy of the catalyst according to the first aspect of the invention;

control means for determining the atmosphere of the anaerobic workstation in accordance with the efficacy of the catalyst; and display means for indicating the atmosphere status of the anaerobic workstation.

A catalyst with a substantially high efficacy will generate sufficient catalytic activity so as to substantially remove oxygen from the anaerobic workstation and thereby create and substantially maintain the anaerobic conditions of the anaerobic workstation. Thus, the control means may be configured to determine the anaerobic workstation has an anaerobic atmosphere when the catalyst is deemed to have substantially high efficacy.

A catalyst with a substantially low (reduced) efficacy generates restricted catalytic activity and so the removal of oxygen is inefficient and the anaerobic conditions of the anaerobic workstation are at risk of becoming compromised. Thus, the control means may be configured to determine the atmosphere of the anaerobic workstation is at risk of becoming compromised when the catalyst is deemed to have reduced efficacy.

Oxygen can not be removed from an anaerobic workstation if the catalyst is an inactive catalyst and so the atmosphere of the anaerobic workstation will become aerobic as oxygen is introduced into the anaerobic workstation. Thus, the control means may be configured to determine the atmosphere of the anaerobic workstation is compromised when the catalyst is deemed to be inactive.

The display means may comprise means for indicating the anaerobic conditions of the anaerobic workstation are being maintained if the catalyst is determined to have a substantially high efficacy. The display means may comprise means for indicating the anaerobic conditions of the anaerobic workstation is at risk of becoming compromised if the catalyst is determined to have a substantially low efficacy. The display means may comprise means for indicating the anaerobic conditions of the anaerobic workstation are compromised if the catalyst is determined to be inactive.

A fourth aspect of the invention relates to a method of monitoring the atmosphere of an anaerobic workstation, the method comprising the steps of:

measuring the temperature of a catalyst used to remove oxygen from the atmosphere by reaction with hydrogen;

determining the efficacy of the catalyst in accordance with any temperature change of the catalyst when oxygen is present in the anaerobic workstation;

determining the atmosphere of the anaerobic workstation in accordance with the efficacy of the catalyst; and displaying the atmosphere status of the anaerobic workstation.

Preferably, the method further comprises using a system according to the third aspect of the invention to monitor the atmosphere of the anaerobic workstation.

DESCRIPTION OF THE DRAWINGS

For a better understanding of the invention, and to show how the same may be carried into effect, reference will now be made, by way of example, to various specific embodiments of the different aspects of the invention as shown in the accompanying diagrammatic drawings, in which.

DETAILED DESCRIPTION OF THE INVENTION

An anaerobic workstation is supplied with an anaerobic gas mixture to provide an anaerobic atmosphere within the workstation. The anaerobic gas mixture typically comprises 80-85% nitrogen gas, 10% carbon dioxide gas and 5-10% hydrogen gas. The nitrogen gas is an inert, inexpensive gas that is provided to make up the balance of the atmosphere. The carbon dioxide gas acts as a growth stimulant for anaerobes. The hydrogen gas is provided to help to create and maintain the anaerobic conditions by combining with any oxygen in the atmosphere of the workstation.

Figure 1:
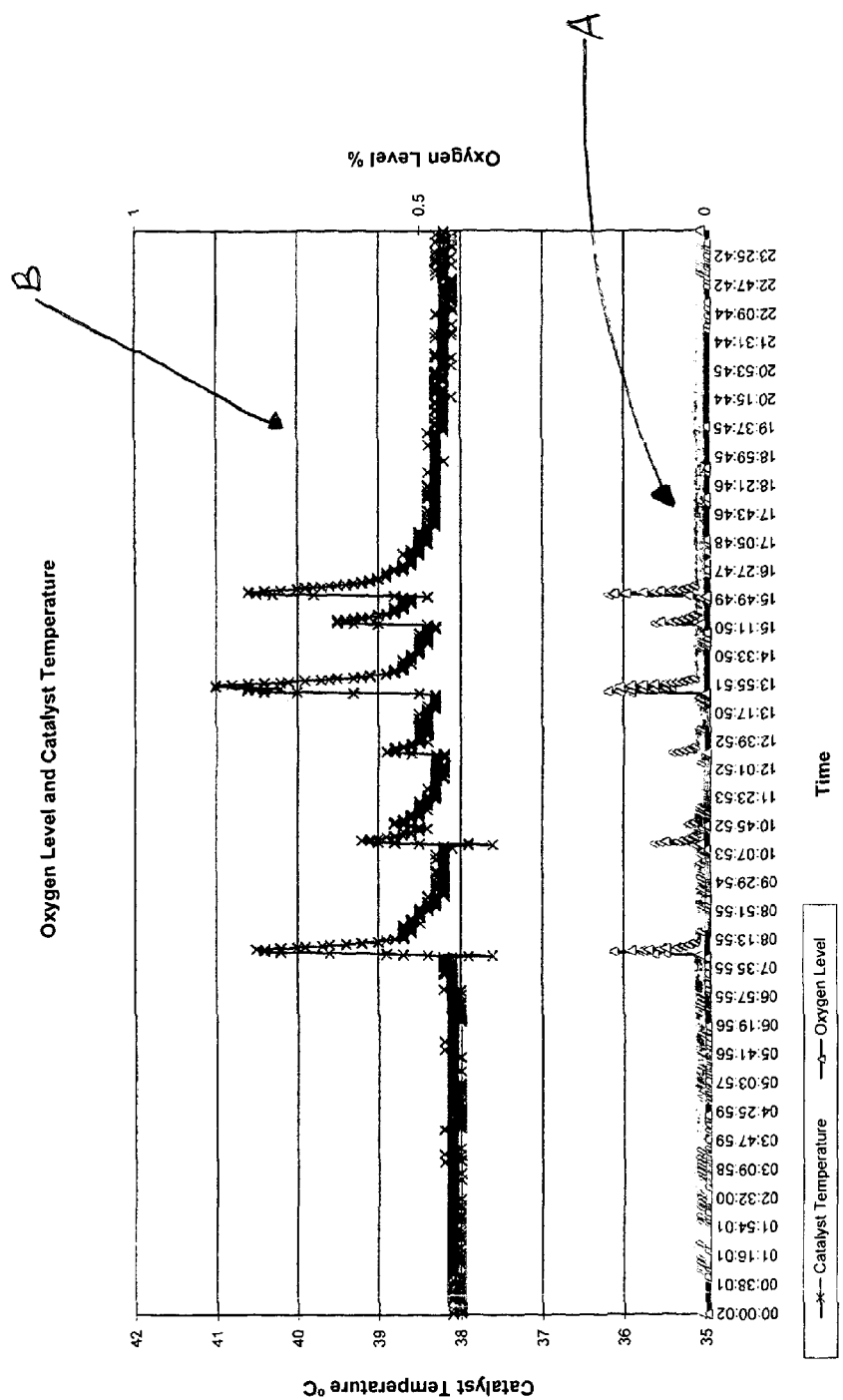
FIG. 1 is a graph showing the relationship between an increase in oxygen level (plot A) in an anaerobic workstation and corresponding increase in catalyst temperature (plot B)

The hydrogen combines with oxygen in the presence of a catalyst. Anaerobic workstations typically use a palladium catalyst to initiate the catalytic reaction to combine oxygen and hydrogen. The catalytic reaction is an exothermic reaction. The amount of heat generated by the catalyst is dependent on the type of catalyst and volume of oxygen to be removed. FIG. 1 shows the relationship between an increase in oxygen level in the anaerobic workstation and the corresponding increase in catalyst temperature during catalytic activity. In FIG. 1 the lower plot marked A shows the oxygen level, the higher plot marked B shows the temperature. It can be seen in FIG. 1 that the temperature rise of the catalyst is generally proportional to the volume of oxygen being combined with the hydrogen. As an example, the temperature of the catalyst may rise by approximately 1-4° C. for each 0.1% volume of oxygen removed. The catalytic activity ceases once the available oxygen has been removed and the catalyst cools to its nominal temperature.

During the catalytic reaction, the hydrogen and oxygen combine in a ratio of 2:1 so as to form water vapour. The water vapour provides moisture in the anaerobic workstation to helpfully ensure the samples do not dry out during incubation. Any surplus water may be removed using extraction means.

When an anaerobic workstation is taken from room atmospheric conditions to an operation state, the catalytic reaction between the hydrogen of the anaerobic gas mixture and the oxygen already present in the workstation causes a significant temperature rise in the catalyst. Depending on the proportions of the gasses connected to the workstation the temperature rise can vary from between 60-130° C.

However, the catalyst is not only able to eliminate oxygen present in the anaerobic workstation when initially commissioned—it can also continuously remove any traces of oxygen introduced into the anaerobic workstation during use. For example, the catalyst is able to remove oxygen that is introduced into the anaerobic workstation when samples are transferred into and out of the workstation, to remove oxygen generated as a by-product of anaerobic growth and/or to remove oxygen naturally present on the skin of the hands of a user.

To maintain stringent anaerobic conditions, it is necessary for the catalyst to remain an active (effective) catalyst; i.e. a catalyst that has the efficacy (capacity) to initiate a catalytic reaction that is sufficient to remove any oxygen present in the workstation.

However, the efficacy of the catalyst of an anaerobic workstation degrades during use. The efficacy of the catalyst may be diminished if the working surface area of the catalyst becomes restricted (e.g. by extraneous matter), if the catalyst is in the presence of volatile fatty acids and/or hydrogen sulphide and/or if the catalyst becomes wet. This degrading of the catalyst has the effect of slowing the rate of catalytic reaction and thereby the rate at which oxygen is removed from the workstation. The rate at which heat is generated during the sluggish catalytic reaction is also correspondingly reduced.

If sufficiently "poisoned", the catalyst may even fail and thereby become an inactive catalyst. The catalyst may fail if it is exposed to sulphur, chlorine compounds, oil, unsaturated hydrocarbons, the vapours of some organic solvents and/or certain metabolic by-products of aerobes. The failure of the catalyst is irreversible and invariably sudden and complete. The failure of the catalyst is critical because oxygen can no longer be removed from the anaerobic workstation and the atmosphere becomes aerobic. When the anaerobic conditions of the workstation become comprised the anaerobic samples may be irreplaceably lost.

A first aspect of the present invention seeks to provide a system for determining the efficacy of the catalyst so as to ascertain if the catalyst is an active catalyst or an inactive catalyst.

The system for determining the efficacy of the catalyst exploits the direct correlation between a detectable rise in catalyst temperature and chemistry associated with the catalytic reaction. The present invention measures the temperature of the catalyst whilst the anaerobic workstation is in use so as to determine if catalytic activity is taking place. If catalytic activity is taking place and oxygen is being removed then the temperature of the catalyst rises above a nominal temperature. If the catalyst has a substantially high efficacy then the catalytic reaction to remove oxygen will be rapid and the rate at which the temperature of the catalyst increases will be high. If the catalyst is not functioning properly then the catalytic reaction to remove oxygen will be slow and the subsequent temperature rise of the catalyst will be sluggish. This type of catalyst is an active catalyst with a reduced (restricted) efficacy. If the catalyst has failed then no catalytic activity will occur and there will be no temperature rise in the catalyst above the nominal temperature.

Figure 2:
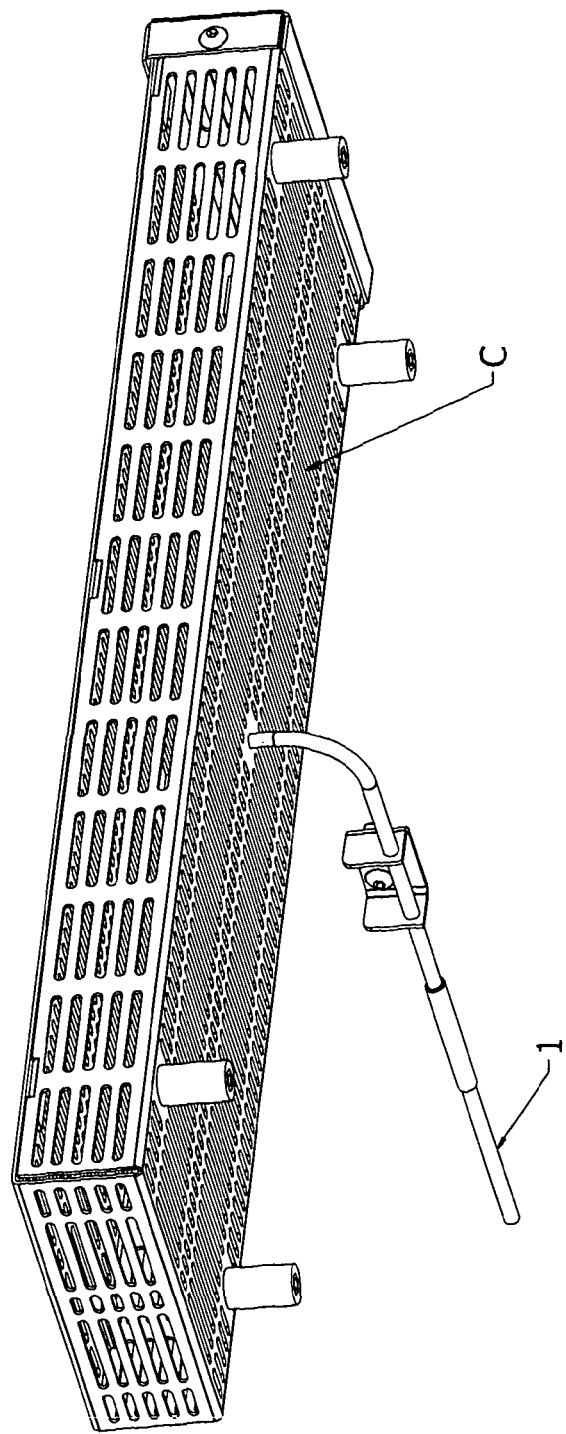
FIG. 2 is a perspective view of an embodiment of a temperature sensing probe located in a catalyst canister.
Figure 3:
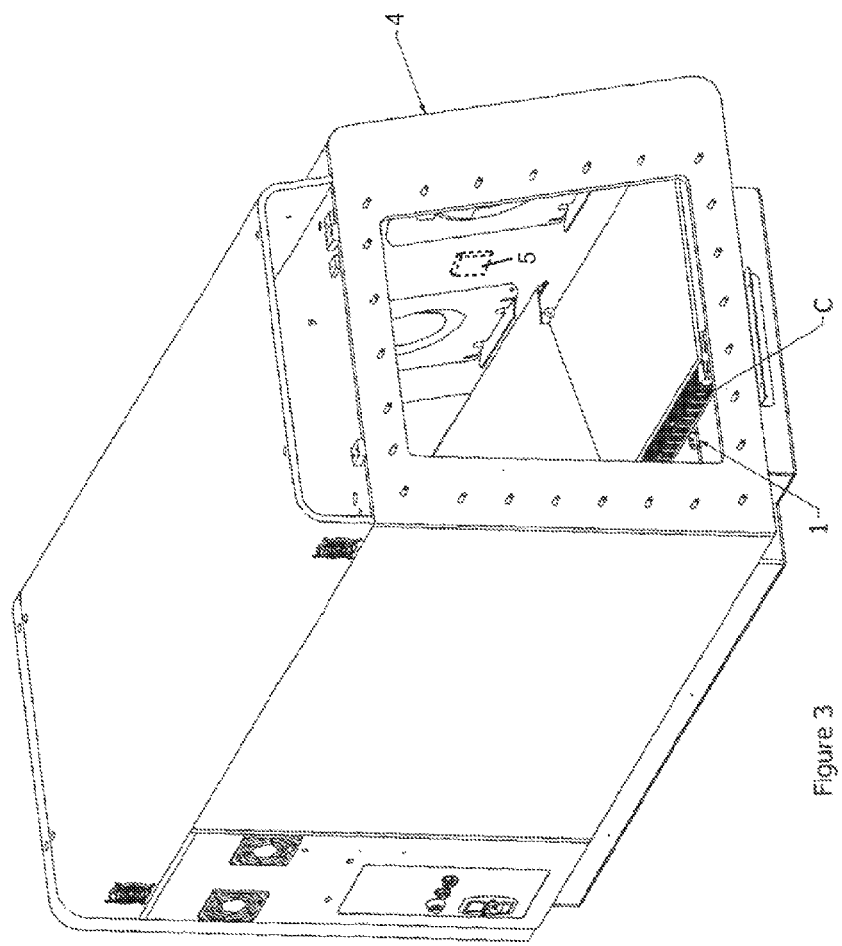
FIG. 3 is a perspective view of the catalyst canister and temperature sensing probe as shown in FIG. 2 located in an anaerobic workstation.
Figure 4:
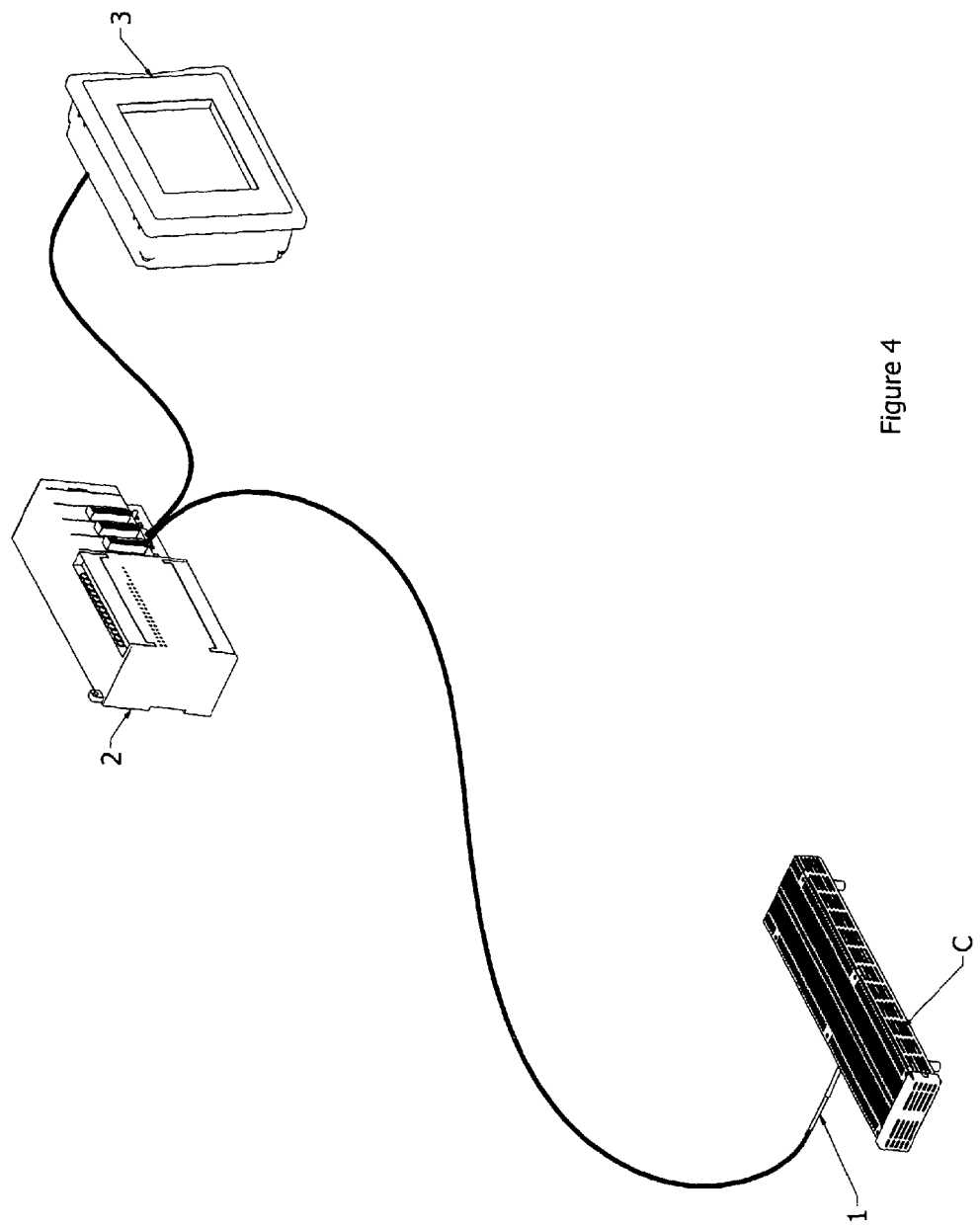
FIG. 4 is a simplistic view of an embodiment of a system or determining the efficacy of the catalyst located in the catalyst canister.

FIGS. 2-4 depict an embodiment of a system for monitoring the catalyst of an anaerobic workstation according to the first aspect of the invention.

The system comprises a temperature probe 1 that is configured to measure the temperature of the catalyst. The temperature probe may be configured to continuously measure the temperature of the catalyst during the operation of the anaerobic workstation. The temperature probe may be configured to intermittently measure the temperature of the catalyst during the operation of the anaerobic workstation.

In the embodiment depicted in FIGS. 2-4, the temperature probe is locatable in the canister C containing the catalyst. The temperature probe is preferably configured such that it may be centrally located in the catalyst canister.

The temperature probe and catalyst canister may be arranged in any suitable location within the anaerobic workstation. As shown in FIG. 3, the temperature probe and catalyst canister may be arranged in an atmosphere flow channel arranged under the floor of the workstation chamber 4.

The temperature probe may be located such that the canister may be mounted on the temperature probe. For example, the temperature probe may be located on the floor of the atmosphere flow channel. When the canister is mounted on the temperature probe, the temperature probe is at least substantially surrounded by catalyst pellets.

The system for monitoring the catalyst comprises a control means 2 for processing the temperature data from the temperature sensing probe to determine the efficacy of the catalyst. It can be seen in FIG. 4 that the temperature sensing means 1 and control means are electrically coupled so that temperature data may be transferred to the control means. The control means may be a programmable logic controller.

The control means is configured to determine the catalyst is an active catalyst if the temperature sensing probe detects a rise in the catalyst temperature above the nominal temperature. The control means is configured to determine the catalyst has high efficacy that is sufficient to remove any oxygen from the anaerobic workstation if the temperature rises above a first predetermined temperature, if the temperature rises by a first predetermined amount or if the temperature increases at a first predetermined rate (a substantially high rate). The control means is configured to determine the catalyst has a low efficacy if the temperature rises above a second predetermined temperature that is lower than the first predetermined temperature, if the temperature rises by a second predetermined amount that is less than the first predetermined amount or if the temperature increase at a second predetermined rate that is slower than the first predetermined rate.

The control means are configured to determine the catalyst is an inactive catalyst if the temperature sensing probe does not detect any rise in the catalyst temperature above the nominal temperature when oxygen is present in the anaerobic workstation.

The embodiment of the system depicted in FIGS. 2-4 further comprises means for displaying the efficacy of the catalyst. The display means may indicate the catalyst is an active catalyst or an inactive catalyst. The display means may comprise means for indicating the catalyst is an active catalyst with a substantially high efficacy, the catalyst is an active catalyst with a substantially low (reduced) efficacy or the catalyst is an inactive catalyst.

The display means may comprise a computer display screen 3. The computer display screen may be a touch screen as depicted in FIG. 4.

Drawing attention to the reduced or absence of catalytic activity will prompt the use to take evasive action to investigate the possible causes and address them. For example, it may prompt a user to change the catalyst of the anaerobic workstation.

The system may further include a means to action a test procedure to determine the efficacy of the catalyst as and when required. The system may include means 5 to introduce a known volume of air (and thus, oxygen) into the workstation. The means may be a sealed vessel of air locatable in the workstation. When released, the system will measure a detectable temperature rise if the catalyst is an active catalyst.

A further aspect of the invention relates to a system for monitoring the atmosphere of an anaerobic workstation. The system determines the atmosphere of an anaerobic workstation in accordance with the efficacy of the catalyst. The system comprises control means to determine the atmosphere of an anaerobic workstation in accordance with the efficacy of the catalyst. The control means may be computer control means. The control means may be a programmable logic controller. The control means for determining the atmosphere of an anaerobic workstation may be the same control means as the control means for determining the efficacy of the catalyst.

A catalyst with a substantially high efficacy will generate sufficient catalytic activity so as to substantially remove oxygen from the anaerobic workstation and thereby substantially maintain the anaerobic conditions of the anaerobic workstation. Thus, the control means may be configured to determine the anaerobic workstation comprises an anaerobic atmosphere and the atmosphere may be sufficiently maintained when the catalyst is deemed to have substantially high efficacy.

A catalyst with a substantially low (reduced) efficacy generates restricted catalytic activity and so the removal of oxygen is inefficient and the anaerobic conditions of the anaerobic workstation are at risk of becoming compromised. Thus, the control means may be configured to determine the atmosphere of the anaerobic workstation is at risk of becoming compromised when the catalyst is deemed to have reduced efficacy.

Oxygen can not be removed from an anaerobic workstation if the catalyst is an inactive catalyst and so the atmosphere of the anaerobic workstation will become aerobic as oxygen is introduced into the anaerobic workstation. Thus, the control means may be configured to determine the atmosphere of the anaerobic workstation is compromised (has become aerobic) when the catalyst is deemed to be inactive.

The system may further comprise display means to indicate the atmosphere of the anaerobic workstation. The display means may comprise means for indicating the anaerobic conditions of the anaerobic workstation are being maintained. The display means may additionally or optionally comprise means for indicating the anaerobic conditions of the anaerobic workstation is at risk of becoming compromised. The display means may additionally or optionally comprise means for indicating the anaerobic conditions of the anaerobic workstation are lost and the workstation is therefore aerobic.

The display means may comprise a computer display screen. The computer display screen may be a touch screen.

Drawing attention to the potentially compromised or compromised atmosphere of the anaerobic workstation will prompt the use to take evasive action to investigate the possible causes and address them. For example, it may prompt a user to change the catalyst of the anaerobic workstation, and/or to investigate whether there is sufficient hydrogen in the atmosphere to react with the oxygen as insufficient hydrogen could be another reason that the catalytic reaction is impaired.

Through out the description and claims of this specification, the words "comprise" and "contain" and variations of the words, for example "comprising" and "comprise", means "including but not limited to, and is not intended to (and does not) exclude other moieties, additives, components, integers or steps.

Throughout the description and claims, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example, of the invention are to be understood to be applicable to any other aspect, embodiment or example described herein unless incompatible therewith.

The invention claimed is:
1. A system for determining the efficacy of a catalyst used to remove oxygen from a controlled atmosphere by reaction with hydrogen, comprising:
   means for introducing a known volume of oxygen into the controlled atmosphere;
   means to detect any temperature change in the catalyst when the known volume of oxygen is introduced into the controlled atmosphere; and control means for processing the detected temperature change to determine the efficacy of the catalyst in accordance with the temperature change.

2. The system of claim 1, wherein the means to detect any temperature change comprises a temperature sensing probe locatable in the catalyst, preferably substantially centrally locatable in the catalyst.

3. The system of claim 1, wherein said control means comprises a computer control means to process temperature data from the temperature sensing means and determine the efficacy of the catalyst based on any temperature change of the catalyst.

4. The system of claim 1, wherein said control means is configured to determine the catalyst is an active catalyst if the temperature sensing means detects a rise in catalytic temperature when oxygen is introduced into the controlled atmosphere.

5. The system of claim 4, wherein the control means is configured to determine the catalyst is an active catalyst with a substantially high efficacy if the temperature sensing means detects the catalyst rises above a first predetermined temperature, if the temperature sensing means detects the catalyst rises by at least a first predetermined temperature change or if the temperature sensing means detects the temperature increases at at least a first predetermined rate of temperature increase when oxygen is introduced into the controlled atmosphere.

6. The system of claim 5, wherein the control means is configured to determine the catalyst is an active catalyst with a substantially low efficacy if the temperature sensing means detects the temperature of the catalyst to rises up to a second temperature that is lower than first predetermined temperature, if the temperature sensing means detects the temperature of the catalyst increases by up to a second temperature change that is less than the first predetermined temperature change or if the temperature sensing means detects the temperature increases at up to a second rate that is slower than the first predetermined rate when oxygen is introduced into the controlled atmosphere.

7. The system of claim 1, wherein the control means is configured to determine the catalyst is an inactive catalyst if the temperature sensing means do not detect a rise in catalytic temperature above a nominal temperature when oxygen is introduced into the controlled atmosphere.

8. The system of claim 1, wherein the system further comprises display means to indicate the efficacy status of the catalyst.

9. The system of claim 8, wherein the control means is configured to determine the catalyst is an inactive catalyst if the temperature sensing means do not detect a rise in catalytic temperature above a nominal temperature when oxygen is introduced into the controlled atmosphere, and wherein the display means comprises means for indicating the catalyst is an active catalyst or an inactive catalyst.

10. The system of claim 9, wherein the display means comprise means for indicating the catalyst is an active catalyst with a substantially high efficacy, the catalyst is an active catalyst with a substantially low efficacy or the catalyst is an inactive catalyst.

11. The system of claim 1 wherein the catalyst is used to maintain an anaerobic environment in an anaerobic workstation.

12. A method of determining the efficacy of a catalyst used to remove oxygen from a controlled atmosphere by reaction with hydrogen, the method comprising:
    detecting a nominal temperature of the catalyst;
    introducing a known volume of oxygen into the controlled atmosphere;
    measuring the temperature of the catalyst after the known volume of oxygen has been introduced into the controlled atmosphere; and
    determining the efficacy of the catalyst with a control means by comparing the nominal temperature to the temperature of the catalyst after the known volume of oxygen has been introduced to determine if the temperature of the catalyst changed when the known volume of oxygen was introduced into the controlled atmosphere.

13. The method of claim 12, further comprising determining that the catalyst is an active catalyst with a substantially high efficacy if the temperature sensing means detects the catalyst rises above a first predetermined temperature, if the temperature sensing means detects the catalyst rises by at least a first predetermined temperature change or if the temperature sensing means detects the temperature increases at at least a first predetermined rate of temperature increase when known volume of oxygen is introduced into the controlled atmosphere.

14. The system of claim 13, further comprising determining that the catalyst is an active catalyst with a substantially low efficacy if the temperature sensing means detects the temperature of the catalyst to rises up to a second temperature that is lower than first predetermined temperature, if the temperature sensing means detects the temperature of the catalyst increases by up to a second temperature change that is less than the first predetermined temperature change or if the temperature sensing means detects the temperature increases at up to a second rate that is slower than the first predetermined rate when oxygen is introduced into the controlled atmosphere.

15. The method of claim 12, wherein the control means is configured to determine the catalyst is an inactive catalyst if the temperature sensing means do not detect a rise in catalytic temperature above a nominal temperature when known volume of oxygen is introduced into the controlled atmosphere.

16. A system for monitoring the atmosphere of an anaerobic workstation and determining the efficacy of the catalyst used to remove oxygen from an atmosphere by reaction with hydrogen, the system comprising:
    means for introducing a known volume of oxygen into the anaerobic work station;
    means to detect any temperature change in the catalyst when the known volume of oxygen is introduced into the anaerobic work station
    control means for processing the detected temperature change to determine the efficacy of the catalyst; and
    display means for indicating the atmosphere of the anaerobic workstation and the efficacy of the catalyst.

17. A system of claim 16 wherein the control means is configured to determine the anaerobic workstation has an anaerobic atmosphere when the catalyst determined to have a substantially high efficacy and the display means is configured to indicate the anaerobic atmosphere status of the anaerobic workstation.

18. A system of claim 16, wherein the control means is configured to determine the atmosphere of the anaerobic workstation is at risk of becoming compromised when the catalyst is determined to have reduced efficacy and the display means is configured to indicate the anaerobic atmosphere status of the anaerobic workstation is at risk.

19. The system of claim 16 wherein the control means is configured to determine the atmosphere of the anaerobic workstation is aerobic when the catalyst is determined to be inactive and the display means is configured to indicate the anaerobic conditions of the anaerobic workstation are compromised.

20. A method of monitoring the atmosphere of an anaerobic workstation, the method comprising the steps of:
- detecting a nominal temperature of the catalyst;
- introducing a known volume of oxygen into the anaerobic workstation;
- measuring the temperature of a catalyst used to remove oxygen from the atmosphere by reaction with hydrogen after the known volume of oxygen has been introduced;
- determining the efficacy of the catalyst with a control means by comparing the nominal temperature to the temperature of the catalyst after the known volume of oxygen has been introduced to determine if the temperature of the catalyst changed when oxygen was introduced into the anaerobic workstation;
- determining the atmosphere of the anaerobic workstation in accordance with the efficacy of the catalyst; and
- indicating the atmosphere status of the anaerobic workstation and the efficacy of the catalyst.

* * * * *